United States Patent [19]

Ishii et al.

[11] Patent Number: 5,962,509

[45] Date of Patent: Oct. 5, 1999

[54] DITHIOLYLIDENE ACETAMIDE DERIVATIVES

[75] Inventors: Fumio Ishii, Sendai; Kinichi Mogi, Narita; Hiromichi Eto, Narita; Susumu Sato, Narita; Hideaki Matsuda, Abiko, all of Japan

[73] Assignee: SSP Co., Ltd., Tokyo, Japan

[21] Appl. No.: 09/169,989

[22] Filed: Oct. 13, 1998

[30] Foreign Application Priority Data

Oct. 17, 1997 [JP] Japan .................................... 9-285076

[51] Int. Cl.$^6$ ...................... A61K 31/385; C07D 339/02
[52] U.S. Cl. .............................................. 514/440; 549/39
[58] Field of Search ................................ 549/39; 514/440

[56] References Cited

FOREIGN PATENT DOCUMENTS 0 298 040  1/1989  European Pat. Off. .
0 460 679  12/1991  European Pat. Off. .

OTHER PUBLICATIONS

Chemical Abstracts, vol. 129, No. 16, 1998, AN 202946f, JP 10 212238, Nov. 29, 1996.

*Primary Examiner*—Deborah C. Lambkin
*Attorney, Agent, or Firm*—Oblon, Spivak, McClelland, Maier & Neustadt, P.C.

[57] ABSTRACT

Disclosed are dithiolylidene acetamide derivatives represented by the following formula:

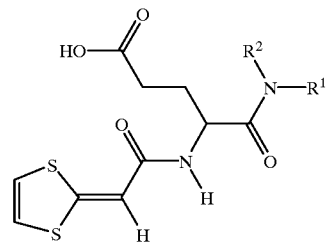

(1)

wherein $R^1$ and $R^2$ may be the same or different and each independently represent a hydrogen atom or an alkyl group, or salts thereof; and pharmaceuticals containing them as effective ingredients. The dithiolylidene acetamide derivatives and their salts show AGE formation inhibitory action and are useful as preventives and therapeutics for diabetic complications.

3 Claims, No Drawings

DITHIOLYLIDENE ACETAMIDE DERIVATIVES

BACKGROUND OF THE INVENTION a) Field of the Invention

This invention relates to novel dithiolylidene acetamide derivatives and salts thereof, and specifically dithiolylidene acetamide derivatives and salts thereof, which have inhibitory action against the formation of advanced glycation end-products (AGE) and are useful as pharmaceuticals for the prevention and treatment of various adult diseases, especially diabetic complications, and also to pharmaceuticals containing them as effective ingredients.

b) Description of the Related Art

A diabetic also tends to develop at a high incidence one or more diabetic complications such as cardiovascular diseases, nephropathy, blindness and/or neuropathic aches, although the mechanisms of their developments have not been elucidated. In recent years, however, both abnormality in polyol pathway and sthenia of glycation have been attracting increasing attention as dysbolism induced by high blood glucose levels. Further, it has become increasingly evident in recent years that the reaction between amino compounds and reducing sugar, said reaction being known in the field of food chemistry, that is, the Maillard reaction proceeds in the living body to glycosylate a surprisingly wide variety of bioproteins and is strongly associated with causes for adult diseases, such as diabetes, and aging. It has been ascertained that this Maillard reaction on the living body results in the gradual formation of advanced glycation end-products (AGE) through complex intramolecular reconstitution. Accumulation of AGE in the body reduces the inherent functions of individual proteins, and is accordingly considered to be one of causes for diseases induced by such reductions, for example, diabetic complications, arteriosclerosis and aging-related diseases such as retinopathy, nephropathy, cardiovascular diseases, neurosis and cataract.

Under continued high blood glucose conditions like diabetes or by aging, many of bioproteins are considered to be subjected to glycation. Among such bioproteins, especially those slow in turnover, for example, collagen, free lens crystallin which does not undergo any turnover, and the like have been proven to undergo the latter-stage Maillard reaction.

As therapeutics for adult diseases, especially diabetic complications, said therapeutics having been developed by paying attention to the Maillard reaction on the living body, the compounds disclosed in JP kokai 9-40626 and JP kokai 9-59233 have been reported but nothing has been put on the market yet. Only aminoguanidine is in the stage of clinical tests.

SUMMARY OF THE INVENTION

An object of the present invention is therefore to provide a compound, which strongly inhibits the formation of AGE and is useful as a preventive and therapeutic for various adult diseases, especially diabetic complications.

With the foregoing circumstances in view, the present inventors synthesized a variety of compounds and proceeded with extensive research on their AGE formation inhibitory action. As a result, it has been found that novel dithiolylidene acetamide derivatives represented by the below-described formula (1) have excellent inhibitory activities against the formation of AGE and are useful as agents for the prevention and treatment of adult diseases, especially diabetic complications, leading to the completion of the present invention.

The present invention therefore provides a dithiolylidene acetamide derivative represented by the following formula (1):

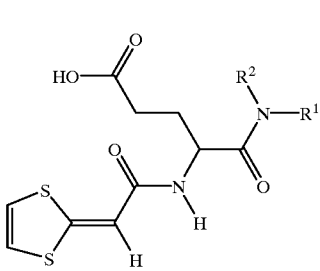

wherein $R^1$ and $R^2$ may be the same or different and each independently represent a hydrogen atom or an alkyl group, or a salt thereof; and a pharmaceutical comprising the dithiolylidene acetamide derivative or the salt thereof as an effective ingredient.

As the dithiolylidene acetamide derivative or the salt thereof according to the present invention shows excellent inhibitory action against the formation of advanced glycation end-products (AGE), it is useful as a pharmaceutical for the prevention and treatment of various adult disease, especially diabetic complications.

Incidentally, as compounds resembling the compounds according to the present invention, dithiolylidene malonate derivatives are known. As raw materials for liquid crystals, a great deal of study is now under way on these dithiolylidene malonate derivatives. In addition, they have been reported to have liver function enhancing effects (JP kokai 63-96184, JP kokai 61-97281, JP kokai 61-10579, etc.) or to have antifungal activities (German Patent No. 25 45 569, etc.). Further, certain dithiolylidene acetamide derivatives similar to the compounds according to the present invention are disclosed to have endothelin antagonism in JP kokai 6-107680 and JP kokai 5-178891. In addition, Tetrahedron, 26(6), 1493–1502 (1970) and Tetrahedron Lett., 28, 2371–2374 (1969) disclose syntheses and reactions of simple amide compounds by way of example.

However, none of the above-described reports contain any disclosure to the effect that they have AGE formation inhibitory action.

DETAILED DESCRIPTION OF THE INVENTION AND PREFERRED EMBODIMENTS

In the dithiolylidene acetamide derivative (1) according to the present invention, the alkyl groups represented by $R^1$ and $R^2$ in the formula (1) may preferably be lower alkyl groups having 1 to 6 carbon atoms, for example, linear or branched $C_{1-6}$ alkyl groups such as methyl, ethyl, n-propyl, i-propyl, n-butyl, i-butyl, sec-butyl, t-butyl, n-pentyl, i-pentyl, n-hexyl or i-hexyl groups. As $R^1$ and/or $R^2$, an n-propyl group is particularly preferred.

No particular limitation is imposed on the salt of the dithiolylidene acetamide derivative (1) according to the present invention insofar as it is a pharmaceutically acceptable salt. Preferred examples of such salts can include hydrogen halides such as hydrofluoride, hydrochloride, hydrobromide and hydroiodide; inorganic salts such as carbonate, nitrate, perchlorate, sulfate and phosphate; lower alkylsulfonates such as methanesulfonate, ethanesulfonate, trifluoromethanesulfonate; arylsulfonates such as benzenesulfonate and p-toluenesulfonate; organic acid salts such as fumarate, maleate, succinate, citrate, tartrate and oxalate; amino acid salts such as glutamate and aspartate; and salts with alkali metals and alkaline earth metals such as sodium, potassium and calcium.

In addition, the present invention also include hydrates, pharmaceutically-acceptable various solvates, polymorphous forms and the like of the dithiolylidene acetamide derivative of the above formula (1). Moreover, the present invention also include stereoisomers of the dithiolylidene acetamide derivative with respect to the asymmetric carbon in the formula (1).

The dithiolylidene acetamide derivative (1) according to the present invention can be synthesized, for example, in accordance with the following scheme.

Synthesis process

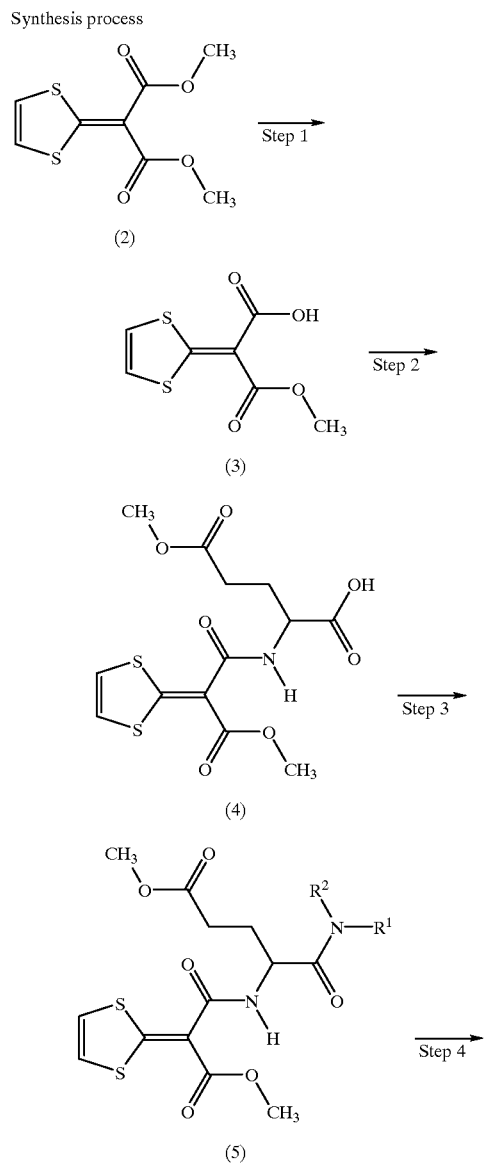

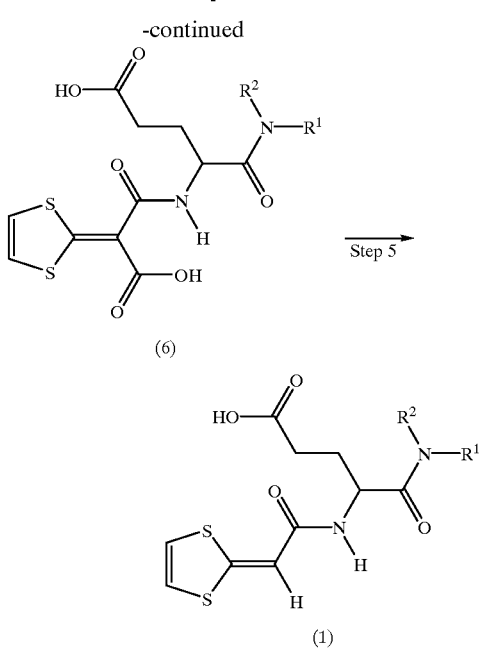

wherein $R^1$ and $R^2$ have the same meanings as defined above.

Namely, the compound (2) is partially hydrolyzed into the compound (3) by using a base (step 1). Methyl glutamate is condensed with the compound (3) to form the compound (4) (step 2). An amine is reacted with the compound (4) so that the compound (5) is obtained (step 3). After the compound (5) is hydrolyzed into the compound (6) (step 4), the compound (6) is decarboxylated, whereby the compound (1) according to the present invention can be produced (step 5). A description will hereinafter be made about each of the steps.

Step 1

The compound (3) can be synthesized by partially hydrolyzing the compound (2) with the base in a solvent. Examples of the base for use in the reaction can include sodium methoxide, sodium ethoxide, potassium t-butoxide, sodium hydroxide, and potassium hydroxide. It is particularly preferred to use 1 equivalent of potassium hydroxide per mole of the compound (2). No particular limitation is imposed on the solvent for use in the reaction insofar as the solvent does not affect the reaction. Examples of the solvent can include water; alcohols such as methanol and ethanol; and mixed solvents thereof. A mixed solvent of water and methanol is preferred. Their mixing ratio may preferably range from 1:1 to 1:9, with 1:8 being especially preferred. The reaction temperature may range preferably from room temperature to the boiling point of the solvent, especially the boiling point of the solvent.

Step 2

The compound (4) can be synthesized by converting the compound (3) into a mixed acid anhydride with ethyl chlorocarbonate, isopropyl chlorocarbonate or the like in the presence of triethylamine and then condensing the mixed acid anhydride with -methyl L-glutamate. Dichloromethane, chloroform or the like is preferred as a solvent. The reaction temperature may be set preferably at −20° C. to room temperature, with 0° C. to room temperature being particularly preferred. Other condensation processes can include a process which proceeds through an acid halide and a process which makes use of a condensing agent such as dicyclohexylcarbodiimide (DCC) or carbonyl diimidazole (CDI).

Step 3

The compound (5) can be synthesized by converting the compound (4) into a mixed acid anhydride with ethyl chlorocarbonate, isopropyl chlorocarbonate or the like in the presence of triethylamine and then condensing the mixed acid anhydride with the amine. Dichloromethane, chloroform or the like is preferred as a solvent. The reaction temperature may be set preferably at −20° C. to room temperature, with 0° C. to room temperature being particularly preferred. Other condensation processes can include a process which proceeds through an acid halide and the process which makes use of a condensing agent such as dicyclohexylcarbodiimide (DCC) or carbonyl diimidazole (CDI).

Step 4

The compound (6) can be synthesized by partially hydrolyzing the compound (5) with the base in a solvent. Examples of the base for use in the reaction can include sodium methoxide, sodium ethoxide, potassium t-butoxide, sodium hydroxide, and potassium hydroxide. It is particularly preferred to use 1 equivalent of potassium hydroxide per mole of the compound (5). No particular limitation is imposed on the solvent for use in the reaction insofar as the solvent does not affect the reaction. Examples of the solvent can include water; alcohols such as methanol and ethanol; and mixed solvents thereof. A mixed solvent of water and methanol is preferred. Their mixing ratio may preferably range from 1:1 to 1:9, with 3:10 being especially preferred. The reaction temperature may range preferably from room temperature up to the boiling point of the solvent, especially the boiling point of the solvent.

Step 5

The compound (1) according to the present invention can be synthesized by decarboxylating the compound (6) in the presence of an acid in a solvent. Examples of the acid can include hydrochloric acid, sulfuric acid and acetic acid, with hydrochloric acid being preferred. Examples of the solvent can include methanol, ethanol, dioxane and tetrahydrofuran, with dioxane being preferred. The reaction temperature may preferably range from room temperature to the boiling point of the solvent, with 50° C. being particularly preferred.

Isolation and purification of the target compounds in the above reactions can be conducted in a manner known per se in the art, for example, by washing, extraction, recrystallization, chromatography and/or the like.

The compound (1) according to the present invention shows excellent AGE formation inhibitory action, so that it is useful as an agent for the prevention and treatment of adult diseases, especially diabetic complications.

To use the compound (1) according to the present invention as such a pharmaceutical, it is only necessary to mix it with a solid or liquid carrier known in the present field of art and then to formulate it into a medicinal composition (medicinal preparation) suitable for parenteral administration, oral administration or external administration.

Examples of the medicinal preparation can include liquid preparations such as injections, inhalants, syrups and emulsions; solid preparations such as tablets, capsules and granules; and external preparations such as ointments and suppositories. These preparations may contain additives commonly employed in the art—such as dissolution aids, stabilizers, humectants, emulsifiers, absorption enhancers and surfactants—as needed. Illustrative of usable excipients are injection-grade distilled water, Ringer's injection, glucose, sucrose syrup, gelatin, edible oil, cacao butter, magnesium stearate and talc.

When the compound (1) according to the present invention is used as an agent for the prevention and treatment of adult diseases, especially diabetic complications, its dose to an adult patient may preferably range from 1 to 1,000 mg per day in the case of oral administration although the dose varies depending on the administration method and the age and weight of the patient. Incidentally, use of the compound (1) of the present invention is not limited to human being, but the compound (1) can also be used for other mammals as a veterinary drug.

The present invention will next be described more specifically by the following Synthesis Examples, Examples and Test. It should however be borne in mind that they are merely illustrative and they by no means limit the present invention.

Synthesis Example 1

Synthesis of 2-(1,3-dithiol-2-ylidene)-3-methoxy-3-oxopropionic acid (3)

Dimethyl 2-(1,3-dithiol-2-ylidene)malonate (2) (116 g) was suspended in methanol (2 l), to which a solution of 33.5 g of 85% potassium hydroxide in water (250 ml) was added. The resulting mixture was heated under reflux for 8 hours. After the solvent was removed, water (2.5 l) was added and the resulting mixture was heated to 50° C. Insoluble matter was filtered off. Concentrated hydrochloric acid (50 ml) was added to the filtrate to acidify the same. The resultant precipitate was collected by filtration and after washing, was dried at 40° C. in air, whereby 2-(1,3-dithiol-2-ylidene)-3-methoxy-3-oxopropionic acid (3) (92 g, yield: 84%) was obtained.

$^1$H-NMR (DMSO-d$_6$, δ): 12.5(1H,br.s), 7.62(2H,s), 3.83 (3H,s).

Melting point: 185–190° C. (decomposed).

Synthesis Example 2

Synthesis of 2-((2-(1,3-dithiol-2-ylidene)-3-methoxy-3-oxopropanoyl)amino)-5-methoxy-5-oxopentanoic acid (4)

2-(1,3-Dithiol-2-ylidene)-3-methoxy-3-oxopropionic acid (3) (109 g) was suspended in dichloromethane (1 l), followed by the addition of 61 g of triethylamine under ice-cooled stirring. To the resulting mixture, ethyl chlorocarbonate (60 g) was added dropwise under ice-cooled stirring over 30 minutes. To a solution of 88.5 g of γ-methyl L-glutamate and 61 g of triethylamine in dichloromethane (1 l), the thus-obtained solution was added dropwise at 10° C. over 1.5 hours. After the resulting mixture was stirred at room temperature for 10 hours, the solvent was removed under reduced pressure. Ethyl acetate (2 l) was added to the residue, and the resultant precipitate was filtered off. After the filtrate was washed with 1 N hydrochloric acid and then with water, the solvent was removed under reduced pressure. The residue was dissolved in methanol (800 ml). Activated carbon (15 g) was added, followed by stirring at 40° C. for 1 hour. The activated carbon was filtered off, and the methanol was removed under reduced pressure. The residue was dissolved in toluene (500 ml) and the toluene was then removed under reduced pressure, whereby 2-((2-(1,3-dithiol-2-ylidene)-3-methoxy-3-oxopropanoyl)amino)-5-methoxy-5-oxopentanoic acid (4) (164 g, yield: 91%) was obtained as a brown oil.

$^1$H-NMR (CDCl$_3$, δ): 8.94(1H,d,J=7Hz), 8.10(1H,br.), 7.20(1H,d,J=6Hz), 7.15(1H,d,J=6Hz), 4.71(1H,q,J=6Hz), 3.95(3H,s), 3.65(3H,s), 2.40–2.60(2H,m), 2.30–2.40(1H,m), 2.10–2.20(1H,m).

Synthesis Example 3

Synthesis of methyl 5-(dipropylamino)-4-((2-(1,3-dithiol-2-ylidene)-3-methoxy-3-oxopropanoyl) amino)-5-oxopentanoate (5)

2-((2-(1,3-Dithiol-2-ylidene)-3-methoxy-3-oxopropanoyl)amino)-5-methoxy-5-oxopentanoic acid (4)

(239 g) was dissolved in dichloromethane (1.5 l), followed by the addition of 70.7 g of triethylamine. To the resulting solution, 71.8 g of ethyl chlorocarbonate were added dropwise at 5–10° C. under stirring over 30 minutes. Subsequent to further stirring at 15–20° C. for 3 hours, di-n-propylamine (70.7 g) was added dropwise at 5–10° C., followed by stirring at room temperature for 12 hours. The solvent was removed under reduced pressure, and ethyl acetate (2 l) was then added to the residue. The resulting precipitate was filtered off. After the ethyl acetate layer was washed with 0.5 N hydrochloric acid and then with water, the solvent was removed under reduced pressure. Diethyl ether (800 ml) was added to the residue and the resulting precipitate was collected by filtration, whereby methyl 5-(dipropylamino)-4-((2-(1,3-dithiol-2-ylidene)-3-methoxy-3-oxopropanoyl) amino)-5-oxopentanoate (5) (113 g, yield: 57%) was obtained as pale yellow crystals.

$^1$H-NMR (CDCl$_3$, δ): 8.89(1H,d,J=8Hz), 7.14(1H,d,J=7Hz), 7.11(1H,d,J=7Hz), 5.10–5.20(1H,m), 3.97(3H,s), 3.67(3H,s), 3.50–3.60(1H,m), 3.40–3.50(1H,m), 3.20–3.30(1H,m), 3.00–3.10(1H,m), 2.30–2.50(2H,m), 2.10–2.20(1H,m), 1.80–1.90(1H,m), 1.50–1.70(4H,m), 0.95(3H,t,J=7Hz), 0.89(3H,t,J=7Hz).

Melting point: 115–117° C.

Synthesis Example 4

Synthesis of 4-((2-carboxy-2-(1,3-dithiol-2-ylidene) acetyl)amino)-5-(dipropylamino)-5-oxopentanoic acid (6)

Methyl 5-(dipropylamino)-4-((2-(1,3-dithiol-2-ylidene)-3-methoxy-3-oxopropanoyl)amino)-5-oxopentanoate (5) (111 g) was dissolved in methanol (1 l), followed by the addition of 2.5 N potassium hydroxide solution (300 ml). The resulting mixture was heated under reflux for 2 hours. The solvent was removed under reduced pressure. The resulting residue was washed several times with water, whereby 4-((2-carboxy-2-(1,3-dithiol-2-ylidene)acetyl) amino)-5-(dipropylamino)-5-oxopentanoic acid (6) was obtained as a waxy substance. Without purification, the reaction product was provided for use in the next example.

EXAMPLE 1

Synthesis of 5-(dipropylamino)-4-((2-(1,3-dithiol-2-ylidene)acetyl)amino)-5-oxopentanoic acid (1)

Dioxane (1.5 l) and activated carbon (10 g) were added to the 4-((2-carboxy-2-(1,3-dithiol-2-ylidene)acetyl)amino)-5-(dipropylamino)-5-oxopentanoic acid (6) obtained in Synthesis Example 4. The resulting mixture was stirred at 50° C. for 30 minutes. The activated carbon was filtered off, and the solvent was removed from the filtrate under reduced pressure. Acetone was added to the thus-obtained residue. The resulting crystals were collected by filtration, washed with water, acetone and diethyl ether, and then dried at 60° C. for 8 hours under reduced pressure, whereby 5-(dipropylamino)-4-((2-(1,3-dithiol-2-ylidene)acetyl) amino)-5-oxopentanoic acid (1) (67 g, yield: 72% (based on the compound (5)) was obtained as pale yellow crystals.

$^1$H-NMR (DMSO-d$_6$, δ): 12.0(1H,br.), 7.78(1H,d,J=9Hz), 6.84(1H,dd,J=1,6Hz), 6.81(1H,d,J=6Hz), 6.28(1H,d,J=1Hz), 4.70–4.80(1H,m), 3.20–3.40(3H,m), 3.00–3.10(1H,m), 2.23(2H,t,J=7Hz), 1.80–1.90(1H,m), 1.50–1.70(3H,m), 1.40–1.50(2H,m), 0.87(3H,t,J=7Hz), 0.80(3H,t,J=7Hz).

Melting point: 220–221° C. (decomposed).

Test 1

Solutions of the test compound shown in Table 1 in dimethyl sulfoxide, said solutions containing said test compound at various concentrations, were each added together with 1 mg/ml of ovolysozyme and 100 mM of xylose to a phosphate-buffered physiological saline of pH 7.4. Each reaction mixture was then incubated at 37° C. for 21 days. A portion of the reaction mixture, said portion being in a predetermined amount, was then separated by sodium lauryl sulfate-polyacrylamide gel electrophoresis (SDS-PAGE). After the electrophoresis, the gel was treated by silver staining to stain proteins. AGE formation inhibitory action of the test compound was calculated in terms of 50% inhibitory concentration by image-processing and analyzing the degree of formation of the dimer (28.8 Kda) of lysozyme (14.4 Kda) relative to that in a control, that is, a reaction mixture not added with the test compound while making use of NIH Image Ver. 1.55. The results are shown in Table 1.

TABLE 1

| Compound | IC$_{50}$ (μg/ml) |
|---|---|
| Example 1 | 30 |
| Amionoguanidine | 30 |

From the above results, the compounds according to the present invention have been found to show inhibitory action against the formation of proteinaceous crosslinks associated with a progress of the Maillard reaction.

This action is comparative with that of aminoguanidine which is a known Maillard reaction inhibitor. The compounds according to the present invention have therefore been found to have extremely high utility as pharmaceuticals for the prevention and treatment of diabetic complications, arteriosclerosis and aging.

This application claims the priority of Japanese Patent Application No. 285076/1997 filed Oct. 17, 1997, which is incorporated herein by reference.

We claim:

1. A dithiolylidene acetamide derivative represented by the following formula (1):

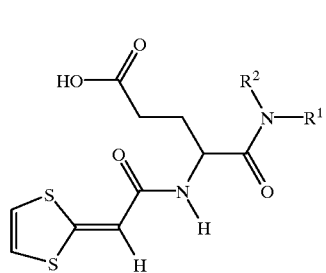

(1)

wherein R$^1$ and R$^2$ may be the same or different and each independently represent a hydrogen atom or an alkyl group; or a salt thereof.

2. A pharmaceutical comprising, as an effective ingredient, a dithiolylidene acetamide derivative or a salt thereof as defined in claim 1.

3. A pharmaceutical according to claim 2, which is an agent for the prevention and treatment of diabetic complications.

* * * * *